United States Patent [19]

Arensdorf et al.

[11] Patent Number: 4,691,697
[45] Date of Patent: Sep. 8, 1987

[54] KNEE SUPPORT

[75] Inventors: Stephen C. Arensdorf; Lawrence T. Stromgren, both of Hays, Kans.; Noel Goudreau, Bourbonnais, Ill.

[73] Assignee: Strom-Tec, Inc., Hays, Kans.

[21] Appl. No.: 720,169

[22] Filed: Apr. 5, 1985

[51] Int. Cl.$^4$ .............................................. A61F 3/00
[52] U.S. Cl. ........................................ 128/80 L; 2/22
[58] Field of Search ............... 128/80 L, 80 R, 80 F, 128/87 R, 83.5, 92 R; 2/22, 24

[56] References Cited

U.S. PATENT DOCUMENTS

| 58,403 | 10/1866 | Goodwin . | |
|---|---|---|---|
| 901,592 | 10/1908 | Clegg . | |
| 1,295,297 | 2/1919 | French . | |
| 1,374,177 | 4/1921 | Barry . | |
| 2,460,895 | 2/1949 | Meany | 2/24 |
| 2,467,907 | 4/1949 | Peckham | 128/88 |
| 3,194,233 | 7/1965 | Peckham | 128/80 |
| 3,350,719 | 11/1967 | McClure, Jr. | 2/22 |
| 3,528,412 | 9/1970 | McDavid | 128/80 L |
| 3,581,741 | 6/1971 | Rosman | 128/80 |
| 3,799,158 | 3/1974 | Gardner | 128/80 L |
| 3,885,252 | 5/1975 | Nakajima | 3/1 |
| 4,097,932 | 7/1978 | Lacey | 2/24 |
| 4,249,524 | 2/1981 | Anderson | 128/80 |
| 4,256,097 | 3/1981 | Willis | 128/80 L |
| 4,312,335 | 1/1982 | Paniell | 128/80 L |
| 4,381,768 | 5/1983 | Erichsen et al. | 128/80 L |

OTHER PUBLICATIONS

Newspaper article from USA Today, entitled "Modern Techniques Tackle Football's Biggest Crippler."
Magazine column from People entitled "Knee Braces are the Best Friends that a Bad—or Good—Knee Ever Had."

Primary Examiner—Robert P. Swiatek
Assistant Examiner—John G. Weiss
Attorney, Agent, or Firm—D. A. N. Chase

[57] ABSTRACT

A prophylactic knee support(s) including a planar impact bar attached to upper and lower mounting bars. The upper and lower mounting bars are fastened to portions of the leg above and below the knee of the user by wraps encircling the appropriate leg portions. Shock absorbers and pressure plates are associated with the impact and mounting bars so as to absorb and dissipate forces resulting from blows directed on the impact bar. The absorption and dissipation diminishes the effect of the blow on the knee including the possibility of undesirable lateral shifting and/or twisting of the knee in response to said blow.

3 Claims, 14 Drawing Figures

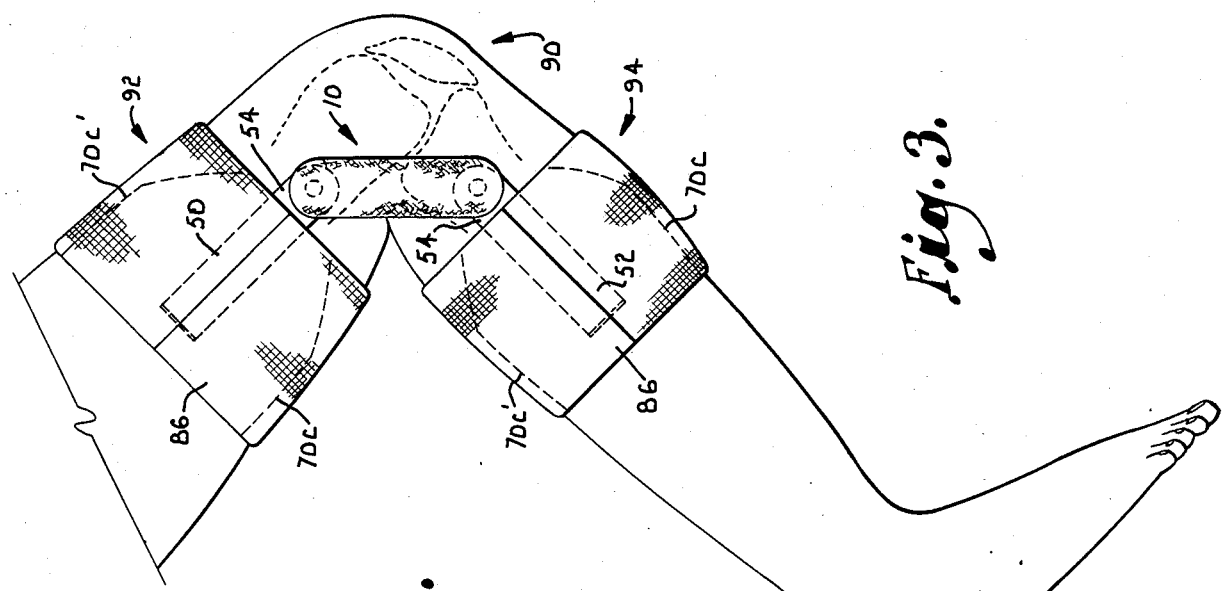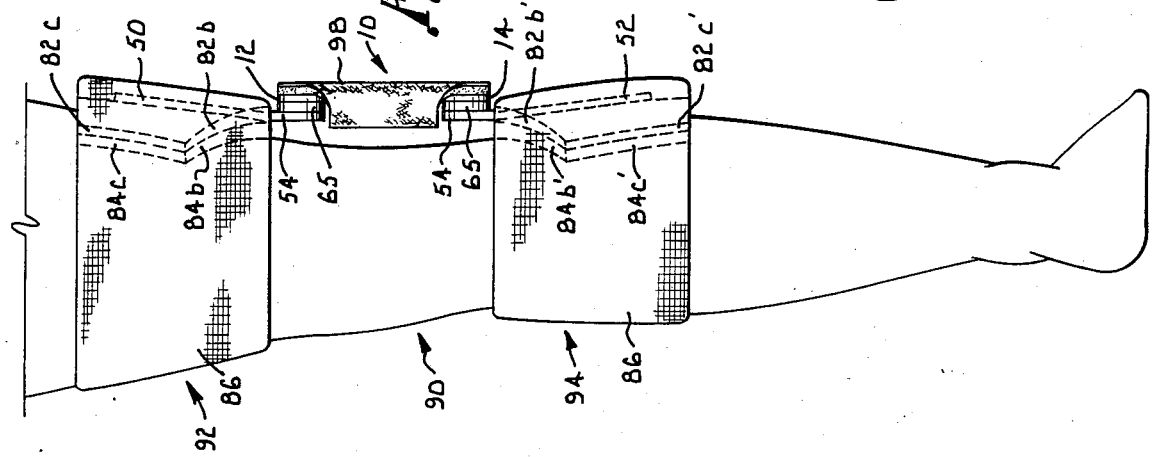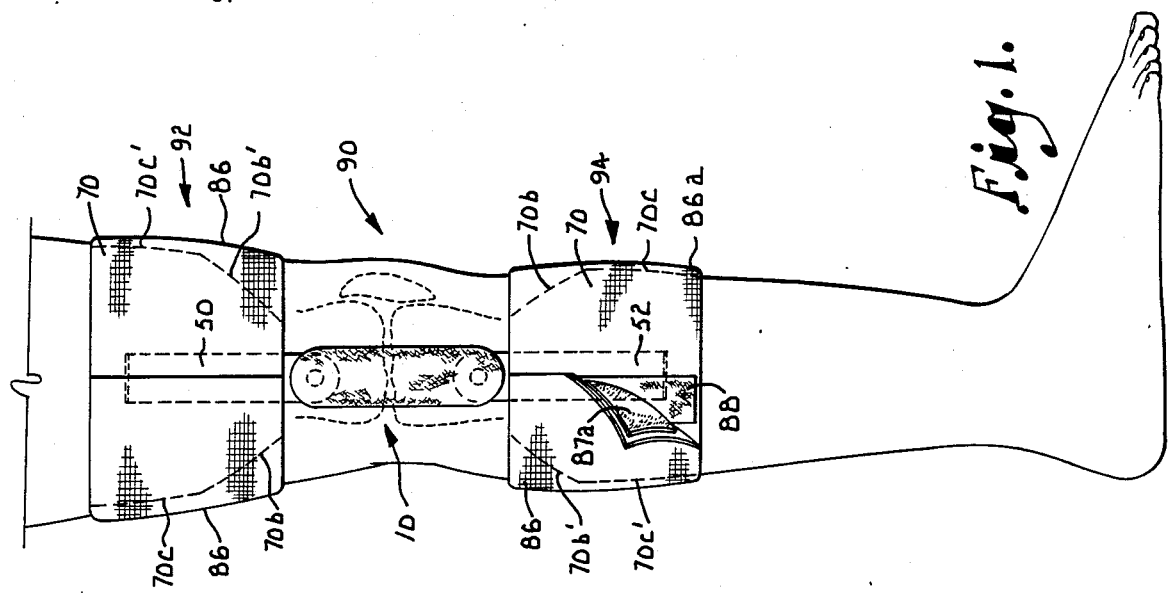

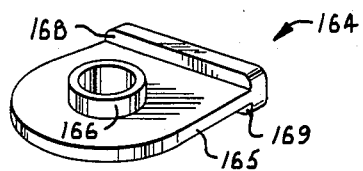
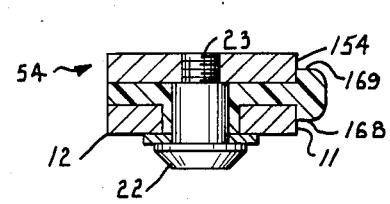
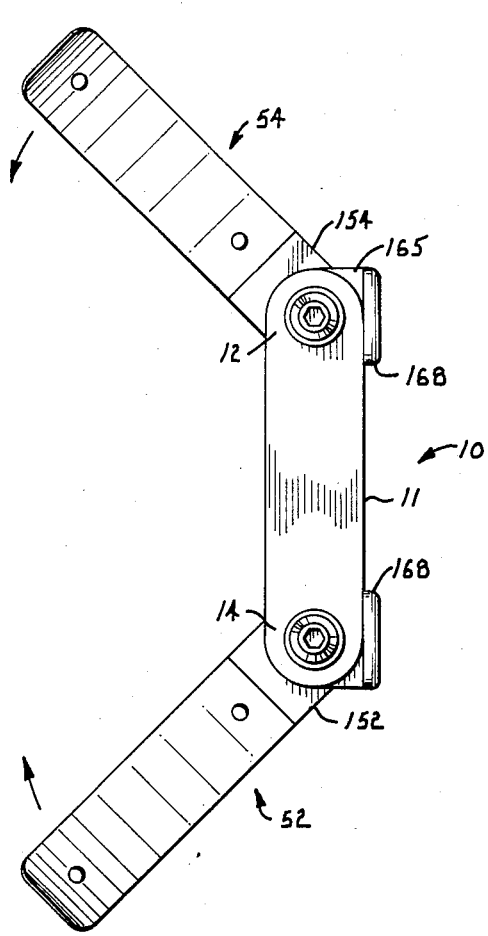
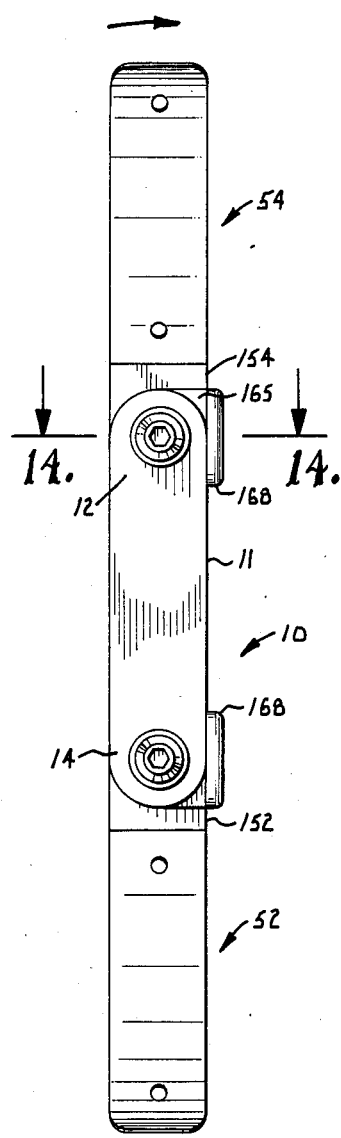
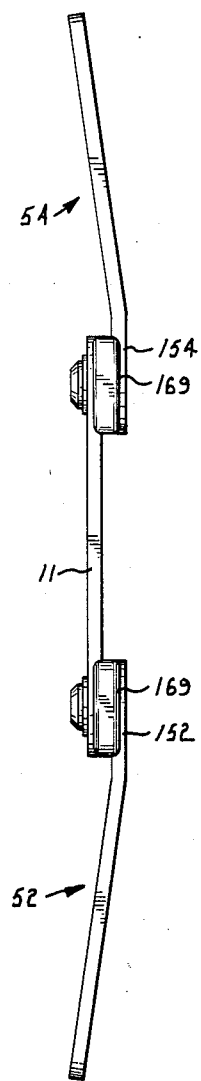

KNEE SUPPORT

BACKGROUND OF THE INVENTION

This invention relates to an improved knee support and more particularly to a prophylactic protection device particularly designed to dissipate the forces arising from blows occuring on the outside of the knee.

Various knee injuries occur when the knee receives a heavy blow at the outer side which forces the knee joint to bend or pivot in a lateral direction. As this lateral knee movement is contrary to the normal knee movement, damage to the tendons and cartilage within the knee can result. Accordingly, various knee braces have been designed for supporting and protecting the knee so as to resist the tendency of the knee joint to buckle or pivot in a lateral direction.

Although past devices have been assumably effective in their operation, little concern has been given to the dissipation of the impacting forces away from the knee proper. If these impacting forces are not properly dissipated, the brace can collapse which in turn can damage the adjacent knee. Furthermore, the forces must be positively directed and/or dissipated away from the knee in order to preclude the undesirable lateral/pivotal movement of the knee joint. Finally, it is desirable to further dissipate the resulting forces throughout the knee support so as to scatter the transmission of these forces onto the leg areas below and above the knee proper.

In response thereto, we have invented a knee support which utilizes a protective impact bar and associated pressure plates for absorbing and dissipating the forces delivered onto the knee. A planar impact bar is pivotally attached at its terminal ends to upper and lower mounting bars which are configured to extend along the leg portions above and below the knee proper. Shock absorbers in the form of resilient washer-like members are interposed between the impact bar and mounting bars to initially absorb and dissipate the forces delivered on the impact bar. Velcro straps encircle the upper and lower leg portions and mounting bars to secure the support to the user's leg. Two embodiments of the knee support both utilize the addition of novel pressure plates, covered with a foam absorbing material, which are particularly designed to dissipate the forces acting on the planar impact bar throughout relatively large areas away from the knee. This dissipation of forces diminishes the effect of the impacting forces and the tendency of the knee to undesirably shift and/or twist in response thereto.

Accordingly, it is a general object of this invention to provide a knee support which efficiently dissipates forces directed on the knee proper to outlying areas.

Another object of this invention is to provide a knee support, as aforesaid, which utilizes particularly designed shock absorbing/dissipating elements therein.

Still a further object of this invention is to provide a knee support, as aforesaid, which includes a planar impact bar pivotally attached to upper and lower mounting bars.

A more particular object of the invention is to provide a knee support, as aforesaid, which utilizes the addition of pressure plates which are particularly designed to dissipate forces away from the knee proper.

Other objects and advantages of this invention will become apparent from the following description taken in connection with the accompanying drawings, wherein is set forth by way of illustration and example, an embodiment of this invention.

BRIEF DESCRIPTION OF THE DRAWINGS

FIG. 1 is a side view of a straight right leg of the user with a first embodiment of the knee support in place.

FIG. 2 is a rear view of the leg and knee support shown in FIG. 1.

FIG. 3 is a side view of the right leg of the user with the knee support in place and leg flexion being shown.

FIG. 10 is a perspective view of an alternate embodiment of a nylon shock absorber for insertion between the impact and respective mounting bars.

FIG. 11 is a side elevation view illustrating the pivotal connection of the upper and lower mounting bars to the impact bar with the alternative shock absorbers therebetween.

FIG. 12 is a side elevation view of the apparatus shown in FIG. 11 and illustrating the locking of the upper and lower mounting bars by the shock absorbers as set forth in FIG. 10.

FIG. 13 is a front view of the apparatus shown in FIG. 12.

FIG. 14 is a sectional view, taken along line 14—14 in FIG. 12, illustrating the attachment of the upper mounting bar to the impact bar with the alternative shock absorber therebetween.

DESCRIPTION OF THE PREFERRED EMBODIMENT

Figures 4, 5, 6:
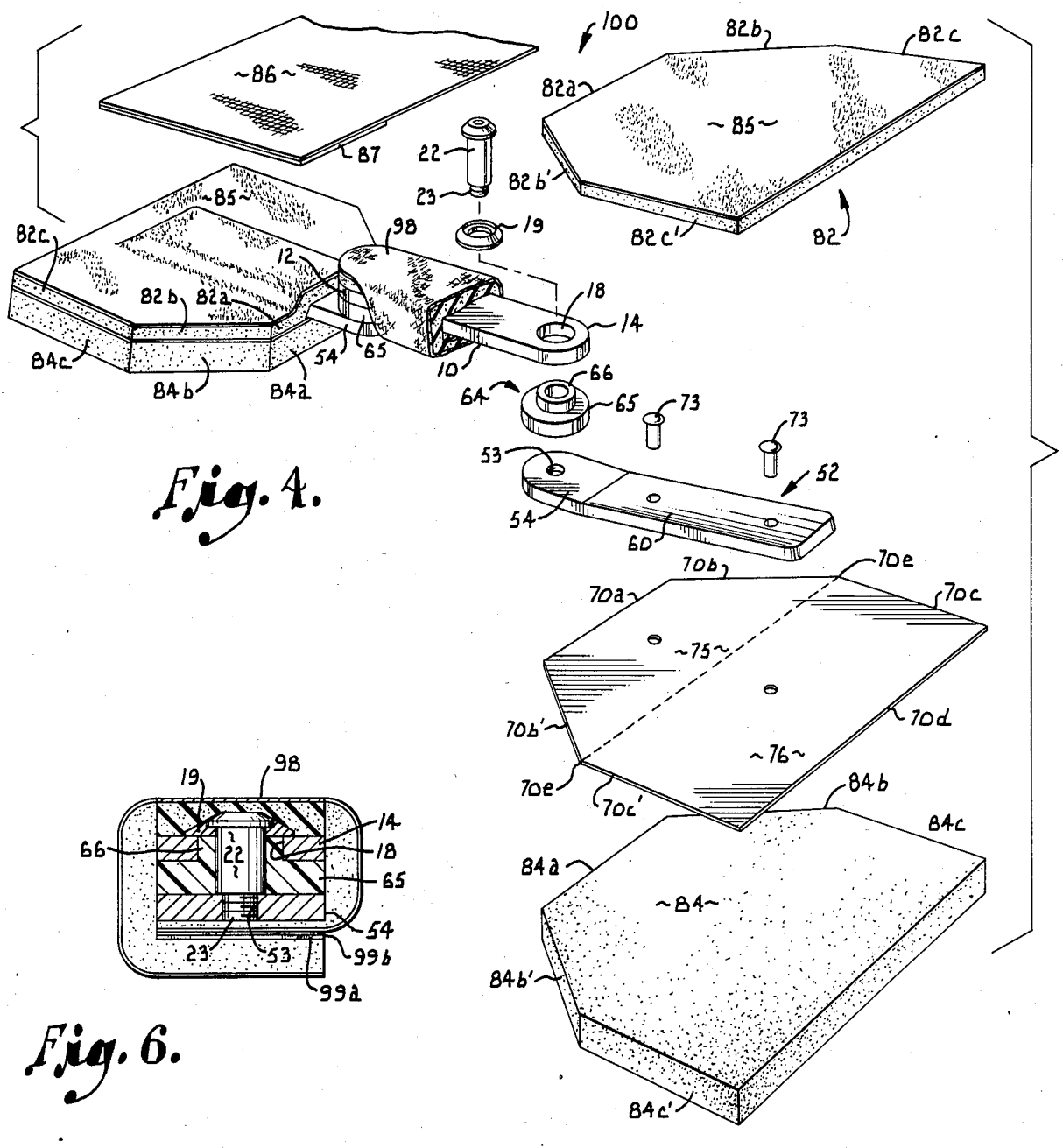
FIG. 4 is a perspective view of the knee support in FIG. 1 with the lower portion thereof being exploded for the purposes of illustration.
FIG. 5 is a side elevation view of the knee support in FIG. 4 with the lower portion thereof being medially sectioned to show the combination of elements therebetween.
FIG. 6 is a sectional view, taken along line 6—6 in FIG. 5, and showing the connection of the shock absorber between the planar impact bar and a mounting bar.

Turning more particularly to the drawings, the first embodiment 100 of the knee support, as shown in FIGS. 1-6, comprises a rigid, planar metal impact bar 10 having first 12 and second 14 integral free ends therein. Apertures 18 in each end 12, 14 of the impact bar 10, having nested brass washers 19 therein, receive pivot pins 22 therethrough. As shown in FIG. 6, each pivot pin 22 has a threaded free end 23 of a reduced diameter which functionally engages the tapped apertures 53 of each mounting bar 50, 52.

First and second metal mounting bars 50, 52 are pivotally attached to the ends 12, 14 of the impact bar 10 by means of the pivot pins 22. Each mounting bar 50, 52 has a planar mounting flange 54 and an integral, canted leg 60 extending therefrom. The cant of each leg 60, relative to the mounting flange 54, is designed to follow the cant of the upper 92 and lower 94 portions of the human leg as they respectively extend in up and down directions away from the knee proper 90. This construction allows the legs 60 of the upper and lower mounting bars 50, 52 to follow the lines of the corresponding leg portions 92, 94 so as to act as mounting flanges in a manner to be subsequently explained.

Inserted between each end 12, 14 of the planar, impact bar 10 and the mounting flanges 54 of the mounting bars 50, 52 are nylon shock absorbers 64 (0.25 inches). Each absorber 64 comprises a cylindrical disk 65 and a coaxial head 66 of a reduced diameter extending therefrom. As shown in FIG. 6, the head 66 extends into each aperture 18 of the impact bar 10 so as to receive the respective pivot pin 22 coaxially extending therethrough. Disk 65 is positioned between the ends 12, 14 of impact bar 10 and the mounting flange 54 of the respective mounting bars 50, 52. Each shock absorber 64 primarily absorbs and dissipates the impacting forces directed onto the impact bar 10 prior to transfer of the forces along mounting bars 50, 52. Secondarily, each absorber 62, 64 reduces the friction about pivot pin 22 and between the ends 12, 14 of the impact bar 10 and mounting flanges 54 during pivotal movement of the impact bar 10 and/or mounting bars 50, 52.

Riveted 73 to the surface of the leg section 60 of each mounting bar 50, 52, facing the leg portion 92 or 94, is a six-sided pressure plate 70 made of copolymer plastic approximately 0.040 inches thick. The pliability of each pressure plate 70 allows it to conform to the upper 92 and lower 94 leg portions upon attachment of the knee support 100 to the leg of the user. It is noted that each plate 70 is of an area which covers the outside area of the respective leg portions 92, 94 extending between the anterior and posterior thereof. Also, each pressure plate 70 presents a short side 70a adjacent the knee 90 proper and a longer side 70d furthest away from the knee proper. This construction presents a first section 75 on the pressure plate 70, as defined by sides 70a, 70b, 70b' and an imaginary line extending between corners 70c and 70c'. A second section 76 extends beyond this imaginary line and to the furthest side 70d. As such, the area of section 75, immediately adjacent the knee 90, is less than the area of section 76. In our now preferred embodiment, the length of each side 70a, 70b (70b') and 70c (70c') is 3.00 inches (7.62 cm) with 45° angles being formed between sides 70a and 70b (70b') and between sides 70b (70b') and 70c (70c').

Congruent, foam absorption pads 82, 84 are then adhered to the opposed sides of each pressure plate 70. A single, unitary foam pad may also be molded about the attached pressure plate 70 so as to present foam sides 82, 84. Preferably, the thickness of foam pad/side 84, which lies adjacent the leg portions 92 or 94, is one-half inch (1.27 cm) with the thickness of the exterior foam pad/side 82 being approximately one-eighth inch (0.32 cm).

Atop the exterior foam pad 82 is fastened a sheet of Velcro-like loop elements 85. Upper and lower elongated wraps 86, have complementary Velcro hook-like elements 87 attached at the ends thereof with one end 87 functionally engaging these loop elements 85 on the exterior foam 82. Upon placing the canted legs 60 of the mounting bars 50, 52 adjacent the upper 92 and lower 94 leg portions, the wrap 86 is wound about the respective legs 60 and leg portions 92, 94. The Velcro elements 87a at the opposed end of wrap 86 then engages a facing complementary Velcro 88 strip on wrap 86. It is understood that the entire wrap 86 may also be made of a material suitable for complementary, releasable engagement with the Velcro elements 87a.

Upon fastening the wrap 86 about the leg and mounting bars 50, 52, the knee support 100 is attached to the leg as shown in FIGS. 1–3. Note that the planar impact bar 10 spans the outside of the knee proper 10 in both FIGS. 1 and 3 with the pressure plates 70 extending between the anterior and posterior of the upper 92 and lower 94 leg portions. A padded protective cover 98, having complementary Velcro elements 99a, 99b at the ends thereof, is then wrapped about the impact bar 10.

In use the pivotal impact bar 10 extends across the knee 90 as shown in the straight leg of FIG. 1 and during leg flexion as shown in FIG. 3. Once the padded 98 impact bar 10 initially receives a blow directed on the knee 90 from the exterior side thereof, the resulting forces are initially absorbed and dissipated by the shock absorbers 64. This initial absorption/dissipation delimits the probability of fracture and/or collapse of the impact bar 10 and subsequent undesirable contact of the bar against the knee proper 90.

These resulting forces are further transmitted along the mounting bars 50, 52 and to the upper and lower polygonal pressure plates 70. These pressure plates 70 present a relatively large area throughout which the resulting forces are absorbed and dissipated. These scattered forces are then transmitted through the absorbent foam 84 prior to transfer to the adjacent leg portions 92, 94. The dissipation of these forces over these relatively large pressure plates 70 delimits the probability that the initial blow will laterally shift and/or twist the knee in undesirable directions. It is again pointed out that the tapered configuration of each plate 70 presents a shorter edge 70a adjacent the knee relative to the upper, longer edge 70d furthest displaced from the knee 90. Thus, the surface area of each plate immediately adjacent the knee, i.e. the first section 75 as above-described, is less than the area of the second section 76 further displaced from the knee as above-described. Thus, the forces dissipated by the pressure plates 70 onto the leg portions 92, 94 are less at the area immediately adjacent the knee 90. This relatively is believed to be effective in further delimiting undesirable movement of the knee 90 resulting from the initial blow.

Figure 7:
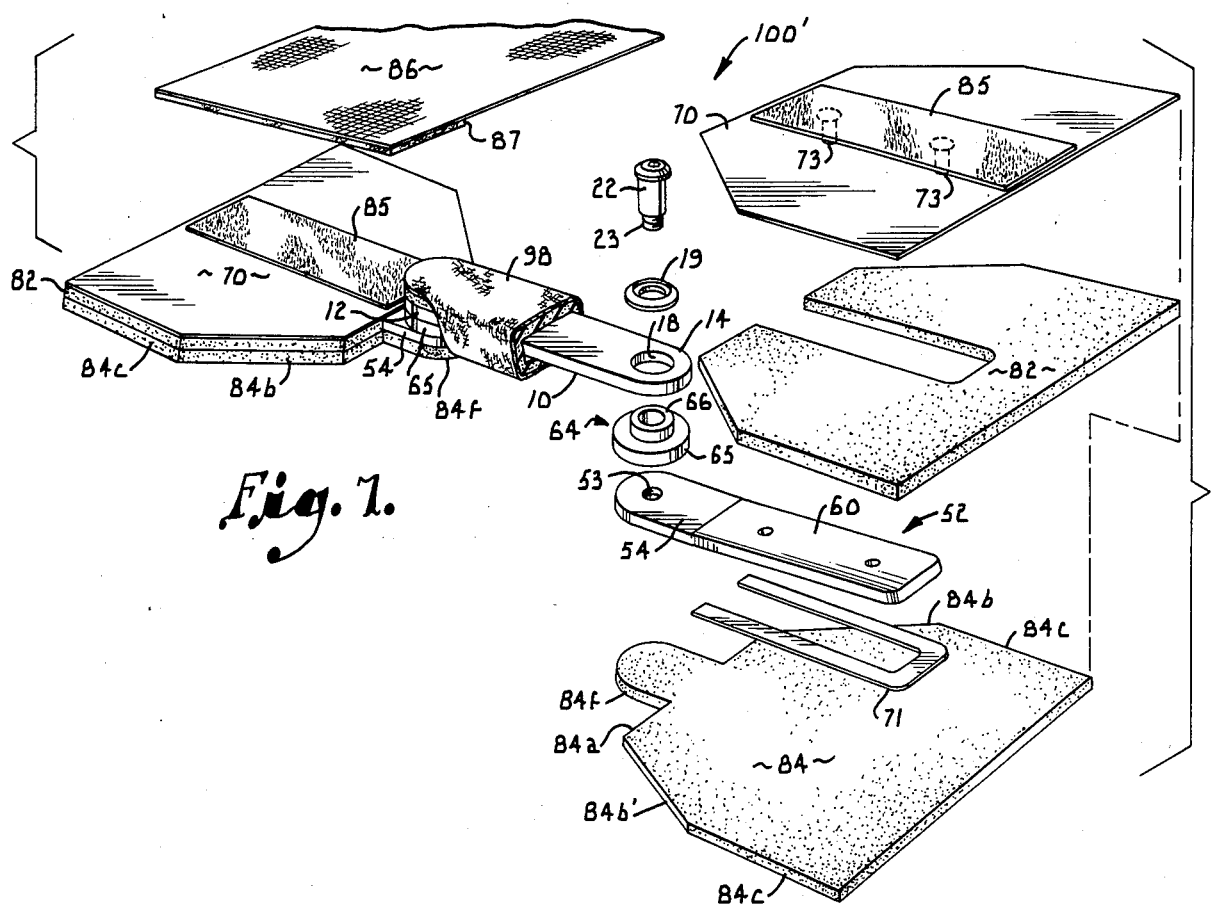
FIG. 7 is a perspective view of a second embodiment of the knee support with the lower side thereof being exploded for purposes of illustration.
Figure 8:
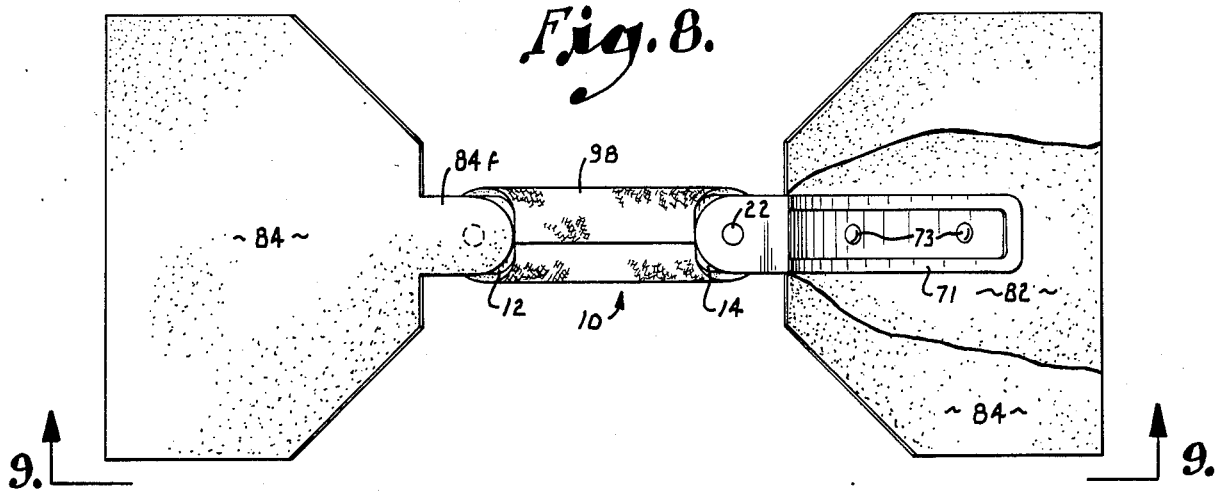
FIG. 8 is a bottom plan view of the unexploded knee support in FIG. 7 with the bottom pad broken away to show the first pressure plate/mounting bar combination.
Figure 9:
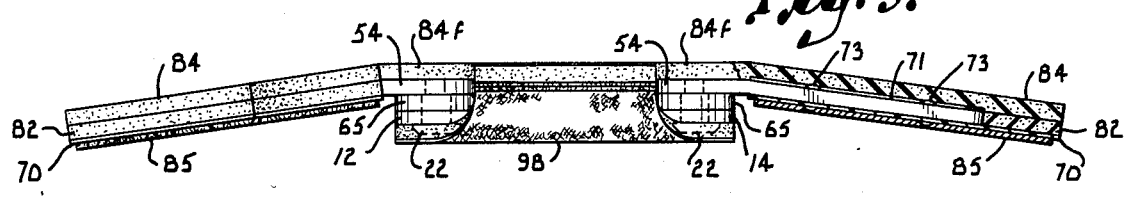
FIG. 9 is a side view, taken along line 9—9 in FIG. 8, with the lower side thereof being medially sectioned to show the combination of elements therebetween.

A second embodiment 100' is as shown in FIGS. 7–9. Therein the same configuration of the impact bar 10 and mounting bars 50, 52 pivotally attached thereto is utilized. This embodiment utilizes a pressure plate assembly which comprises a first horseshoe shaped pressure plate 71 adhesively attached to the interior side of the legs 60 of the respective mounting bars 50, 52. Again first 82 and second 84 foam pads are adhered to opposed sides of the pressure plate 71 and respective mounting bars 50, 52. The foam pad 82 has a horseshoe cutout allowing for protrusion of the opposed side of the leg 60 of the mounting bars 50, 52 therethrough. Positioned atop the second foam pad 82 and riveted 73 to the leg 60 of the respective mounting bars 50, 52 are the polygonal pressure plates 70 as shown in the first embodiment. The rivets 73 are covered by a strip of Velcro loop elements 85 glued to the exterior face of the pressure plate 70.

Accordingly, a pressure plate assembly comprising the pressure plates 70 and 71 is associated with each of the respective mounting bars 50, 52. The knee support 100' is then attached to the leg by means of wraps 86 as above-described and in the manner as shown in FIGS.

1-3. Again forces delivered to the outside of the knee are first absorbed/dissipated by the impact bar 10 and the associated shock absorbers 64. The forces are then transmitted along the mounting bars 50, 52 for dissipation throughout the polygonal pressure plates 70 and pressure plates 71. The foam pads 82 and 84 both of which are now interposed between the polygonal pressure plate 70 and adjacent leg portions 92, 94 enhances the absorption of the previously dissipated forces being directed onto the respective leg portions 92, 94. Again, the initial forces on the impact bar 10 are dissipated away from the knee area 90 in a manner similar to embodiment 100 so as to delimit the tendency of the knee to laterally move and/or twist in undesirable directions and the resulting knee injury attributable thereto.

FIGS. 10-14 illustrate an alternative embodiment 164 of the shock absorbers 64 set forth in FIGS. 1-9. Each absorber 164 is made of a nylon or similar material. The shock absorber 164 comprises a disk member 165, approximately 0.0125 inches (0.32 mm) thick with a cylindrical head 166 protruding therefrom. First and second ridges 168, 169 extend in opposed, normal directions beyond the front edge of the planar disk 165.

As shown in FIG. 14, the absorber 164 is mounted between the end of the upper mounting bar 54 and the end 12 of the impact bar 10 by means of a pivot pin 22 extending through aligned apertures in the mounting bar 54, impact bar 10 and the cylindrical head 166. The threaded portion 23 of pivot pin 22 engages the tapped aperture in the upper mounting bar 54. Identical structure is utilized for the pivotal connection of the lower mounting bar 52 to the end 14 of the impact bar 10 with the alternative shock absorber 164 therebetween.

The outwardly extending ridge member 168 of each absorber 164 contacts the front edge 11 of the impact bar 10. This ridge 168/front edge 11 abutment positions the opposed ridge 169 at a selected point in the pivotal path of the lower 52 and upper 54 mounting bars. The opposed, interiorly extending ridge 169 of each absorber 164 contacts the front edge 152, 154 of the lower 52 and upper mounting bars 54 when the respective bars 52, 54 are pivoted to points approaching the position shown in FIG. 12. This edge 152, 154/ridge 169 abutment precludes further rotation of the lower 52 and upper 54 mounting bars about the respective pivot pin 22 in respective counterclockwise and clockwise directions, as viewed in FIG. 12. This abutment precludes further rotation of the mounting bars 52, 54 in said directions to undesirable points beyond the impact bar 10 which may cause a harmful hyperextension of the attached knee 90. However, as shown in FIG. 11, the pivotal movement of the lower 52 and upper 54 mounting bar in desirable clockwise and counterclockwise direction, is not hindered by the locking ridges 169 of the respective absorbers 164.

It is to be understood that while certain forms of this invention have been illustrated and described, it is not limited thereto, except in so far as such limitations are included in the following claims.

Having thus described the invention, what is claimed as new and desired to be secured by Letters Patent is:

1. A knee support for attachment to a leg of the user to protect the knee, said support comprising:
   a rigid impact bar having upper and lower ends;
   an upper mounting bar adapted to lie adjacent said leg above the knee;
   a lower mounting bar adapted to lie adjacent said leg below the knee;
   means pivotally connecting said upper end of the impact bar to said upper mounting bar, and pivotally connecting said lower end of the impact bar to said lower mounting
   upper pressure plate means on said upper mounting bar adapted to be secured to the user's leg above the knee;
   lower pressure plate means on said lower mounting bar adapted to be secured to the user's leg below the knee, whereby said impact bar may be positioned in laterally spaced, spanning relationship to the knee;
   shock-absorbing, anti-friction means between said upper and lower ends of the impact bar and the respective upper and lower mounting bars, comprising upper and lower bushing members interposed between said ends of the impact bar and the respective mounting bars at said pivotal connections;
   a ridge on said upper bushing member projecting therefrom and engageable with a front edge of said impact bar and said upper mounting bar upon movement thereof to a position selected to prevent further movement and hyperextension of the knee; and
   a ridge on said lower bushing member projecting therefrom and engageable with said front edge of the impact bar and said lower mounting bar upon movement thereof to a position selected to prevent further movement and hyperextension of the knee.

2. The knee support as claimed in claim 1, wherein each of said bushing members has a flat, disk-like configuration, each of said ridges being rigid with a front edge of the associated bushing member.

3. The knee support as claimed in claim 2, wherein each of said ridges includes first and second ridge members projecting from opposed faces of the associated bushing member at its front edge engagement with said impact bar and the corresponding mounting bar.

* * * * *

UNITED STATES PATENT AND TRADEMARK OFFICE
CERTIFICATE OF CORRECTION

PATENT NO. : 4,691,697
DATED : September 8, 1987
INVENTOR(S) : STEPHEN C. ARENSDORF et al It is certified that error appears in the above—identified patent and that said Letters Patent is hereby corrected as shown below:

Claim 1, Column 6, line 19, after "mounting" add --bar;--.

Claim 3, Column 6, line 53, after "edge" add --for--.

Signed and Sealed this

Twenty-second Day of March, 1988

Attest:

DONALD J. QUIGG

*Attesting Officer*    *Commissioner of Patents and Trademarks*